(12) United States Patent
Su et al.

(10) Patent No.: US 7,922,327 B2
(45) Date of Patent: Apr. 12, 2011

(54) APPARATUS AND METHOD FOR ILLUMINATING AND VIEWING THE ANTERIOR SEGMENT OF AN EYE OF A PATIENT

(75) Inventors: Wei Su, Sunnyvale, CA (US); Norbert A. Massie, San Ramon, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 781 days.

(21) Appl. No.: 11/581,020

(22) Filed: Oct. 13, 2006

(65) Prior Publication Data

US 2007/0030446 A1 Feb. 8, 2007

Related U.S. Application Data (60) Continuation of application No. 11/158,426, filed on Jun. 22, 2005, now Pat. No. 7,121,665, which is a division of application No. 10/758,695, filed on Jan. 15, 2004, now Pat. No. 6,921,169, which is a continuation of application No. 10/033,432, filed on Dec. 26, 2001, now Pat. No. 6,685,317, which is a continuation of application No. 09/592,899, filed on Jun. 13, 2000, now Pat. No. 6,361,167.

(51) Int. Cl.
*A61B 3/10* (2006.01)
(52) U.S. Cl. .................................................. 351/205
(58) Field of Classification Search .................. 351/205, 351/208; 600/310
See application file for complete search history.

(56) References Cited

U.S. PATENT DOCUMENTS

| 4,235,540 | A | | 11/1980 | Hanamura et al. |
| 4,443,075 | A | | 4/1984 | Crane |
| 5,202,709 | A | * | 4/1993 | Ichihashi et al. ............. 351/208 |
| 5,279,298 | A | | 1/1994 | Flower |
| 5,279,928 | A | | 1/1994 | Dedio et al. |
| 5,346,689 | A | | 9/1994 | Peyman et al. |
| 5,394,199 | A | | 2/1995 | Flower |
| 5,467,104 | A | | 11/1995 | Furness, III et al. |
| 5,620,436 | A | | 4/1997 | Lang et al. |
| 5,757,462 | A | | 5/1998 | Nanjo |
| 5,892,569 | A | | 4/1999 | Van de Velde |
| 5,912,720 | A | * | 6/1999 | Berger et al. ................. 351/206 |
| 5,983,120 | A | * | 11/1999 | Groner et al. ................. 600/310 |
| 5,993,001 | A | | 11/1999 | Bursell et al. |
| 6,120,461 | A | | 9/2000 | Smyth |
| 6,166,496 | A | | 12/2000 | Lys |
| 6,215,957 | B1 | | 4/2001 | Van Houten |
| 6,238,385 | B1 | | 5/2001 | Harino et al. |
| 6,351,663 | B1 | | 2/2002 | Flower et al. |
| 6,392,539 | B1 | | 5/2002 | Kanasugi |
| 6,394,603 | B2 | | 5/2002 | Miwa et al. |
| 6,440,950 | B1 | | 8/2002 | Zelmer |

(Continued)

OTHER PUBLICATIONS

Sommer, et al., "Cross-Polarization Photography of the Nerve Fiber Layer", Arch Opthalmol article, vol. 102, Jun. 1984.

(Continued)

*Primary Examiner* — George Manuel
(74) *Attorney, Agent, or Firm* — Charles E. Krueger (57) ABSTRACT

A digital camera that combines the functions of the retinal camera and/or corneal camera into one, single, small, easy to use instrument includes features such as image and laser spot stabilization, an LED light source, stereo corneal imaging, polarizing reflection reduction, visual function testing, and so on.

27 Claims, 7 Drawing Sheets

U.S. PATENT DOCUMENTS 6,814,441 B2 11/2004 Ohnuma et al.

OTHER PUBLICATIONS

Fariza, et al., "Use of Circularly Polarized Light in Fundus and Optic Disc Photography", Arch Opthalmol, vol. 106, Jul. 1988.

Eli Peli, M.Sc., O.D., "Circular Polarizers Enhance Visibility of Ednothelium in Specular Reflection Biomicroscopy", Arch Opthalmol article, vol. 103, May 1985.

Kawara, et al., "A New Method for Retroillumination Photography of Cataractous Lens Opacities", American Journal of Opthalmology, vol. 90, No. 2, pp. 186-189, 1980.

MediVision 510(k) premarket notification and letter from Department of Health & Human Services, Oct. 20, 2006.

James B. Pawley, "Handbook of Biological Confocal Microscopy", The Intermediate Optical System of Laser-Scanning Confocal Microscopes, Second Edition, University of Wisconsin-Madison Zoology Department, Chapter 9, Plenum Press, New York and London (Mar. 31, 1995).

* cited by examiner

APPARATUS AND METHOD FOR ILLUMINATING AND VIEWING THE ANTERIOR SEGMENT OF AN EYE OF A PATIENT

RELATED APPLCATIONS

This application is a continuation of Ser. No. 11/158,426, filed Jun. 22, 2005, now U.S. Pat. No. 7,121,665 to issue Oct. 17, 2006, which is a divisional application of Ser. No. 10/758,695, filed Jan. 15, 2004, now U.S. Pat. No. 6,921,169 issued Jul. 26, 2005, which is a continuation application of Ser. No. 10/033,432 filed Dec. 26, 2001, now U.S. Pat. No. 6,685,317 issued Feb. 3, 2004, which is a continuation application of Ser. No. 09/592,899 filed Jun. 13, 2000, now U.S. Pat. No. 6,361,167 issued Mar. 26, 2002. All applications are hereby incorporated by reference for all purposes.

This invention relates to eye cameras and in particular to digital eye cameras.

BACKGROUND OF THE INVENTION

Eye Examinations

Eye health-care practitioners generally divide patient examination into three parts: examination of the cornea, examination of the retina, and a vision function exam including measurement of the refractive status of the eye. The doctor's findings need to be recorded and the standard method for last century has been to make hand-written notes in the chart. Hand recording of vision function and refractive status is completely satisfactory. Vision function is basically a quantitative assessment by the doctor and six numbers describe the refractive information of both eyes so that the manual recording process is quick and efficient. Recording the clinical status of the cornea and retina is completely different.

For the retinal and corneal eye-health exams what is needed is quantitative clinical data but what has usually been recorded in the past is the doctor's clinical assessment. For example, an examiner may record, "the optical disk has a normal pallor" which is the clinical perception or, even more simply, the diagnoses, "this patient does not have glaucoma". Seldom is the actual clinical information recorded, which, in this instance, would be a color image of the optical disk. This lack of documentation leaves open an opportunity for later criticism that the examination or diagnoses was faulty. Further, it is well known in the instance of estimating the pallor, the cup-to-disk ratio, and the like, that making assessments of these quantities are difficult and that the intra-observer variation is large. Especially for these examples, it would be quite beneficial to have a method for making a detailed comparison of changes in the optical disk between exams.

Most retinal exams are accomplished by using the optical aids of the direct ophthalmoscope, binocular indirect ophthalmoscope (BIO) or a special lens with the slit-lamp/biomicroscope.

Direct Ophthalmoscope

The direct ophthalmoscope consists of a light and single lens held between the doctor's and patient's eye by which the doctor can visualize a very small segment of the retina at a time. The light is considered uncomfortably bright by most patients and skill is required on the part of the clinician. By scanning the visualized area about, a mental image of the posterior pole may be obtained for a basic assessment of retinal health. It is difficult to simply stop the scan and study a given area such as the optical disk because of patient motion and discomfort.

Binocular Indirect Ophthalmoscope

For a more complete visualization of the retina, a BIO may be used. The BIO comprises a lens mounted on a headband in front of each of the doctor's eyes, a single lens held by hand close to the patient's eye, and a light also mounted on the doctor's headband. The field-of-view visualized is wider than that of the direct ophthalmoscope and this instrument is generally used through dilated pupils. With the BIO the doctor can more thoroughly examine the periphery of the retina. Using the BIO requires a great deal of clinical skill and is usually learned over a period of an entire year while the doctor is in training. However, like the direct ophthalmoscope, the doctor must develop a mental picture of the broader features of the eye and, because of the bright light and movements of the patient's eye, it is difficult to stop and carefully study one portion of the retina.

Slit-Lamp Biomicroscope

The slit-lamp is designed for corneal visualization. This instrument is a binocular microscope and a small lamp that projects a narrow rectangle of light into the anterior structures. This microscope, with a special lens and the slit-lamp light, can be used for retinal visualization as well. However, when modified for retinal imaging, its inherent limitations generally prevent it from providing high quality retinal visualizations. The examination can only be done on patients with a dilated iris. The lens is positioned to be very close to the patient's eye, which in turn makes it very difficult to determine and adjust the alignment for the lens. The contact type lens can be very uncomfortable to the patients. The lens produces strong light reflection from its surfaces, which deteriorate the quality of retinal image greatly. However, with only a slit of light, only small portions of the retina can be observed at a time and patients generally feel that the light intensity if very uncomfortable. Overall, modifications on the slit lamp biomicroscope produce a very substandard retinal visualization system.

Dilation and Bright Lights

Currently, for a through eye exam, and almost always when the BIO is used, it is necessary to dilate the patient's eye. Dilation comprises the application of eye drops that open the iris to a larger than normal diameter and can not be applied until the refraction portion of the exam is completed. Significant time is required for the drops to take effect. During this time the patient is almost always taking up limited space in the examination room. Further, dilation is very objectionable to patients because of the elapsed time for the dilation to return to normal. Studies show that this alone is a major factor for patients to defer having eye exams. Most patients also find the brightness of the light objectionable and many times to the point of pain. While some BIO's come equipped with head-mounted cameras, these have not been widely accepted, are regarded as difficult to use, and only image a small portion of the retina at a time in any instance. A hazard of dilation is the risk of inducing acute glaucoma that can lead to immediate blindness. Thus, a system that can accomplish an exam with little or no dilating eye drops and no bright light would be of great advantage.

Prior Art Eye Cameras

Fundus Cameras

For accurate documentation sometimes fundus cameras are used as a supplement or replacement for the manual retinal exam. These cameras have been in use since the 1940's and most of them record images of the retina on film. Film has the disadvantage of requiring processing before an assessment of image quality can be obtained and there is no ability to immediately electronically transfer the image. Some cameras are now being equipped with digital imaging add-on capability. By digital imaging we mean the use of an electronic image sensor such as CCD or CMOS followed by digitization and digital storage means.

In current practice these digital add-ons to existing cameras and are quite bulky and expensive. As a consequence, fundus cameras, digital or film, are usually located in a separate room and a specialized technician is employed to operate them. The high level of acquisition and operating costs for digital cameras has left digital imaging to the domain of high-end clinical sites and they are not used for routine exams. Digital cameras have also been added to slit-lamp biomicroscopes so that they can be used for imaging, but this single purpose application has generally proved to not be cost effective and is seldom implemented.

Use of Fundus Cameras for Cornea Viewing

Although designed for retina imaging, the fundus camera has been used to image the cornea. However, the camera generally produces low quality pictures because the inherent achromatic and spherical optical aberrations when used with an air path and are high and the camera has only a very limit working range. When the cornea is in focus, the patient's eye is located so close to the camera that it becomes difficult to place a slit-lamp between them and no known commercial product provides a slit-lamp with the fundus camera. If a slit-lamp were added, the lamp would block or distort the view of camera when it is positioned in the front of the objective lens. The built-in internal magnification adjustment for the fundus camera is not adequately designed for the required magnifications of corneal imaging. Thus, as a practical matter, using the fundus camera for corneal imaging is very non-optimal.

Scanning Laser Ophthalmoscope

In yet another prior art retinal imaging approach, a mechanically driven mirror is used to scan a laser beam about the retina and the reflected intensity is measured to generate an image. These imaging systems, commonly called a scanning laser ophthalmoscope or SLO, usually only provide one laser wavelength and this therefore does not produce a color image, a significant clinical disadvantage. Recently, a system was provided to the market with two laser colors, but even this produces very, very poor color image quality. Even greater limitations are in the relatively long exposure time that allows eye movement during the frame time, the large size, and the high cost.

Prior Art Laser Eye Surgery

The laser has been widely used in treatment of various diseases in the anterior and posterior segment of the eye. The BIO or biomicroscope is one method used to deliver the laser to retinal or corneal region. To align the clinician's eye, the condensing lens and patient's eye must be in line for viewing, and at same time the laser spot must be directed to the intended area. This is a very challenging task. The slit-lamp biomicroscope, with additional laser delivery attachment and a laser lens (contact or noncontact), is the most commonly used platform. Although it provides a more stable condition for laser procedure, the external attachment makes the system complicated to use. The laser lens is very often being held by one hand of the clinician. Any motion of the lens causes the viewed retinal image to move, especially in the case of high magnification lens. It is not comfortable to hold the laser lens steady during the long laser treatment session which can last for several minutes. The regular illumination to the retina is provided by the slit-lamp lamp in this case. To avoid blocking the laser beam the clinician must maintain certain positions with the slit-lamp while simultaneously projecting the light to the desired area. In addition, the reflected laser light from the laser lens can scatter back in many directions in the room, a result hazardous to others present. Viewing through the biomicroscope and laser lens, the clinician can not simultaneously see the iris and make the judgment on the state of alignment for the lens. As result, there is the risk of accidentally firing the laser on to the iris. The nature of the manual manipulation of the laser beam also makes it difficult to assess the dosage of laser being delivered to the retina if no clear marks are left after the treatment. In a new treatment, photodynamic therapy, the laser power level is below that which would leave a mark on the retina. This, the control of the laser dosage is very critical in PDT treatment. Sometimes, a completely separate system is provided for laser treatment, adding to the expense to well equip an eye doctors office.

What is needed is a relatively low cost, digital, and eye camera for monitoring and recording the conditions of the retinal and corneal regions of the eye. This system would have even greater value if it could be additionally used for laser treatment and retinal stimulus for visual function testing.

DETAILED DESCRIPTION OF THE INVENTION

First Preferred Embodiment External Design

Figure 1:
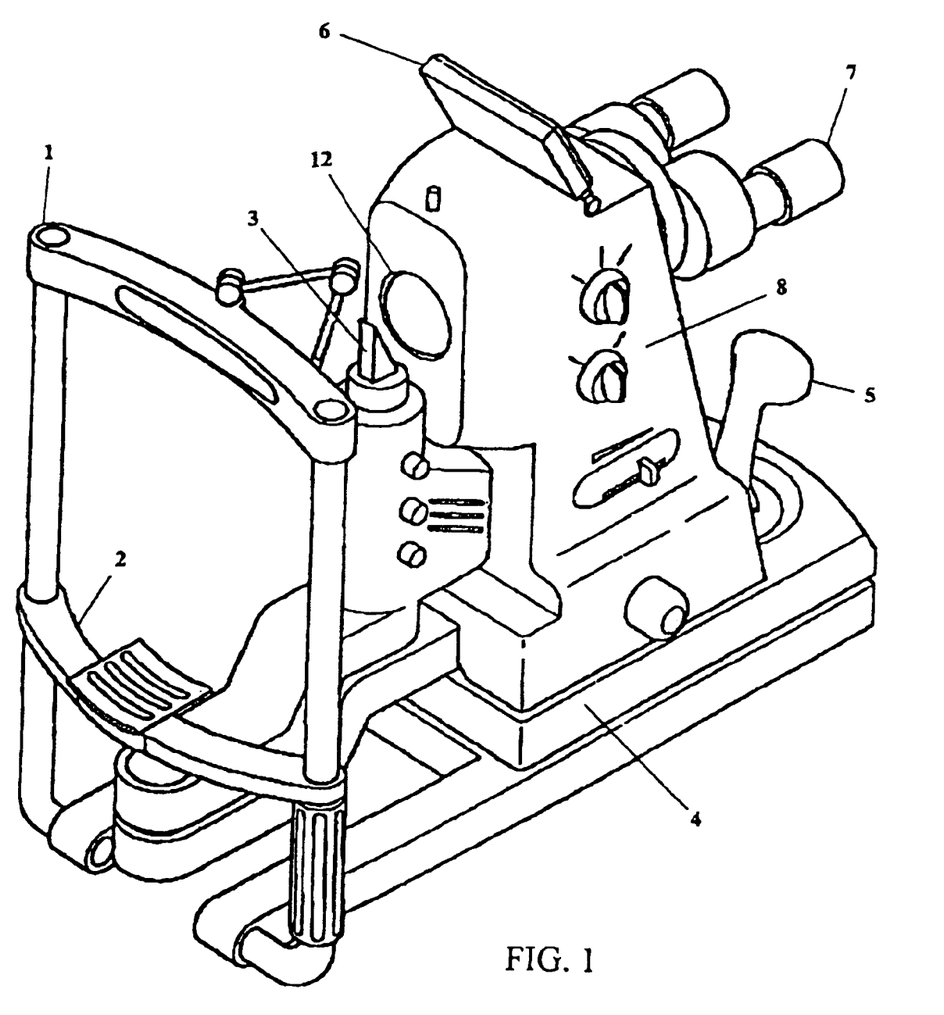
FIG. 1 is a drawing of a preferred embodiment of the invention.

In FIG. 1 is shown the exterior design of a first preferred embodiment of the present invention. A typical headrest 1 and chin rest 2 is provided to stabilize the patient head.

The slit lamp 3 provides illumination for examination of the cornea and is adjustable in brightness, color, and width of slit.

The base 4 provides the usual degrees of freedom in angular, transverse and longitudinal motion. Inside of the camera are means for adjusting the height of the camera potentially through a motorized system. Joystick 5 assists in controlling motion and has control switches for operation of the system. In FIG. 1, the joystick 5 is shown on base 4. Alternatively, the joystick 5 can be mounted on a portable base, and be placed on different position away from the base 4.

A small LCD display 6 can be used to display the image, especially a real-time infrared corneal image. However, the main image display is a larger monitor and is not shown. Oculars 7 are provided for achieving all of the typical visual functions associated with the slit-lamp biomicroscope. Lens 12 is the front objective lens and seals the optical system. Various controls 8 for magnification, light level and the like are located on the side of the camera. The dimensions of the camera are similar to those of the conventional slit-lamp biomicroscope.

Retinal Imaging

Figure 2:
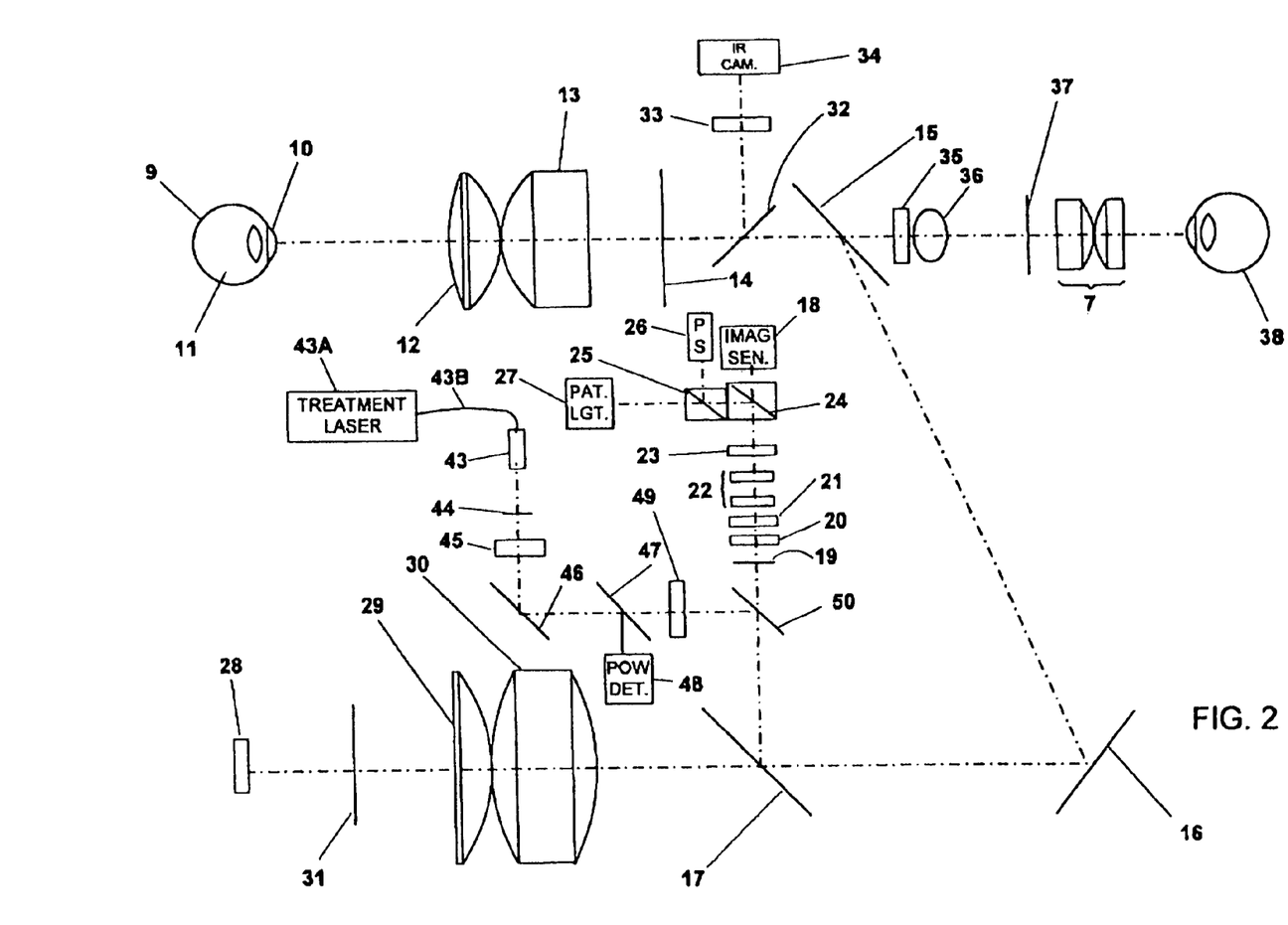
FIG. 2 is a drawing showing the optical layout of the retinal imaging portion of the preferred embodiment.
Figure 2A:
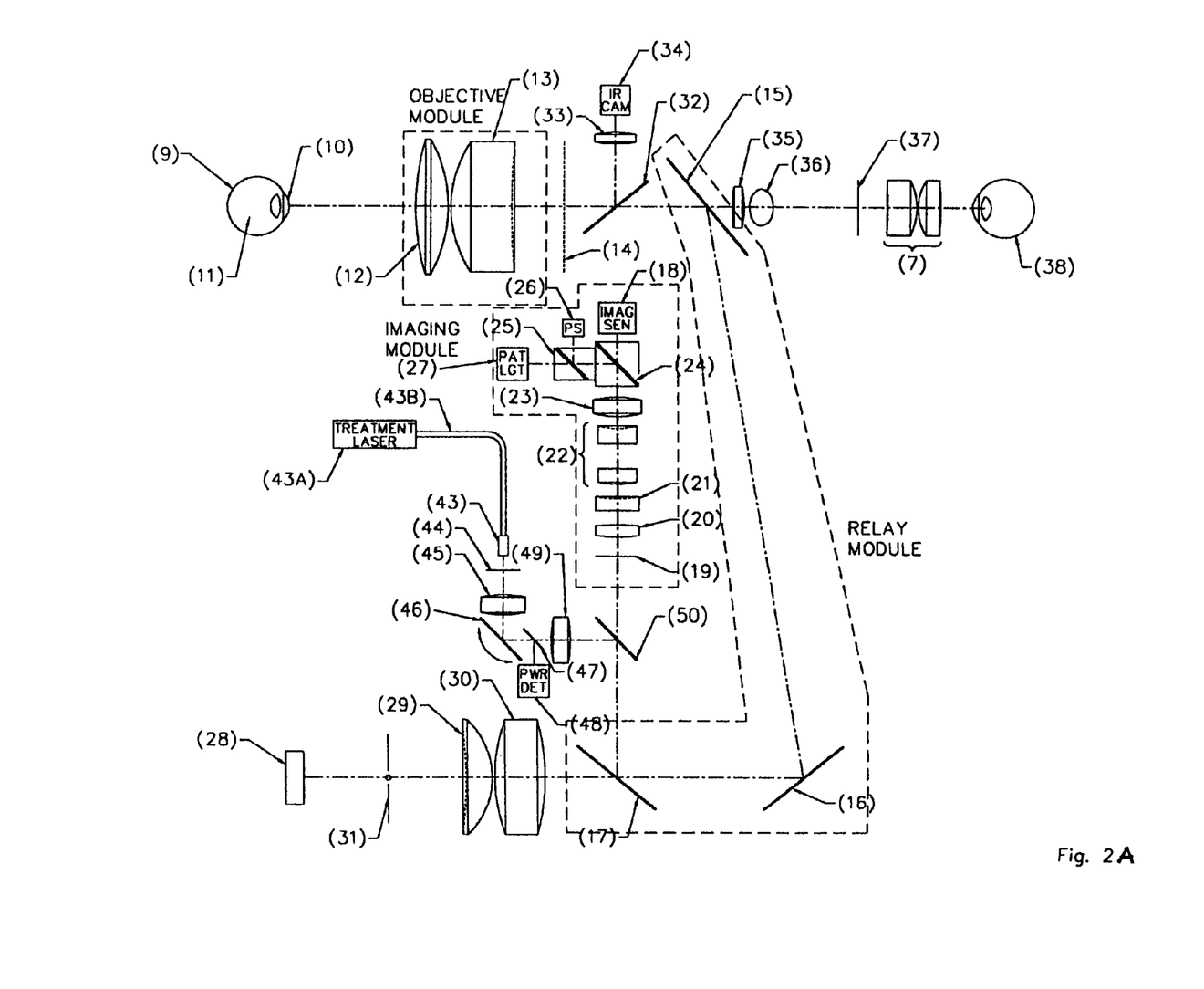
FIG. 2A is a drawing showing the grouping of the elements of FIG. 2 into an objective module, a relay module, and an imaging module.

Referring to FIG. 2, the retina 9 is the back portion of the eye and is a curved object plane. The vitreous 11 is a non-achromatic gel that fills the eye. Thus one challenge of the optical system will be to image the curved plane of the retina through the non-achromatic gel onto the flat plane of the electronic area image sensor, typically CCD or CMOS, and produce high resolution achromatic images though an optical system which compensates for the non-achromaticity of the eye.

The objective lens is comprised of lens elements 12 and 13. The front lens 12 is not changed between the retinal and corneal imaging and seals the optical system. The second objective element 13 is internally changeable and provides for the optical system objective lens changes necessary for switching between the corneal and retinal imaging functions. This also places the lens changing mechanism inside the camera and out of contact with the operator's fingers for safety. The rear objective lens 13 when combined with the front objective lens 12 comprises the objective lens set for retinal imaging. Plane 14 is the location of the first real image and may contain a mask to limit the field of view.

Mirror 15 is switched into place for the retinal-imaging task, and when in place, blocks the view of the visualization section of the slit lamp/biomicroscope comprised of elements 35 through 37 and 7. With the mirror in place the light is directed downwards and is further reflected by mirrors 16 and 17 and directed to image sensor 18. Located at 19 is an aperture that is the optical aperture for the imaging system. This aperture is relayed to the lens of the eye to form the entrance pupil of the camera when in the retinal imaging mode. Lens 20 projects the image at 14 approximately at infinity and lens 21 is movable along the optical axis to focus the image exactly at infinity. Lens set 22 can be inserted or removed to change the magnification of the system.

Finally, lens 23 refocuses the image onto the image sensor 18. By changing lens 23 sensors of various size or format can be utilized by changing only one lens. This is a significant advantage as the sensor for color imaging may have a different size than one optimized for angiography, which might be a larger format sensor operating in a single color. It also allows the system to be retrofitted for new sensors as they may become available.

Beam splitters 24 and 25 partially reflect light from retina 9 onto a photo sensor 26 for auto exposure control. The beam splitter 24 also reflects light from light source 27 into the optical system in such fashion that source 27 is optically conjugate to the retina 9. The source 27 may provide lighting for an internal fixation light and/or an auto focusing mechanism. Or, for example, it could be a programmable LCD so that a varying fixation point could be provided or sources for testing vision could be utilized.

Masks or programmable light sources such as LCD's can be used at 27 to provide for vision function testing. Tests such as perimetry, color sensitivity, contrast sensitivity testing, and the like may be readily provided.

Source 28 provides illumination for retinal imaging and can be pulsed or continues. The source 28 is shaped as a ring of light and the light is injected co-axially by lenses 29 and 30 such that a ring of light is projected onto the eye lens of the patient but outside of the entrance pupil. The illumination light passes through the space outside the mirror 17. By this fashion high contrast images can be obtained. In-plane 31, a small diameter disk shaped optical linear polarizer is placed on the optical axis to polarize, in the plane of the paper, the portion of the illuminating beam that is on axis. There is an unwanted reflection from objective lens 12 and 13 and this reflection will be polarized. The refection from the retina is however depolarizing. This unwanted reflection will only come from the center of the lens because this is the part of the lens where the surface is normal to the outgoing illumination beam. To block the reflection of light from the lens 12 and 13 from entering the electronic camera, polarizing beam splitter 24 reflects the s-polarized light and transmits the p-polarized light. The polarization direction of the linear polarizer at plane 31 is oriented to be normal to that of p-polarization at beam splitter (24).

To accurately align the optical system to the iris on patient's eye, an infrared imaging system consisting of beam sampler 32, lens 33, and infrared camera 34 is inserted into the optical path. The beam sampler 32 is highly transmissive to the visual light and slightly reflective for infrared light. When the cornea portion of the eye is illuminated by an infrared source (not shown in FIG. 2) mounted outside the periphery of lens 12, infrared light is collected by lens 12 and 13, and then sampled by beam sampler 32. Lens 33 forms a corneal image on the camera 34. The image formed on camera 34 can be used to determine the transverse and longitudinal alignment to the eye.

Figure 3:
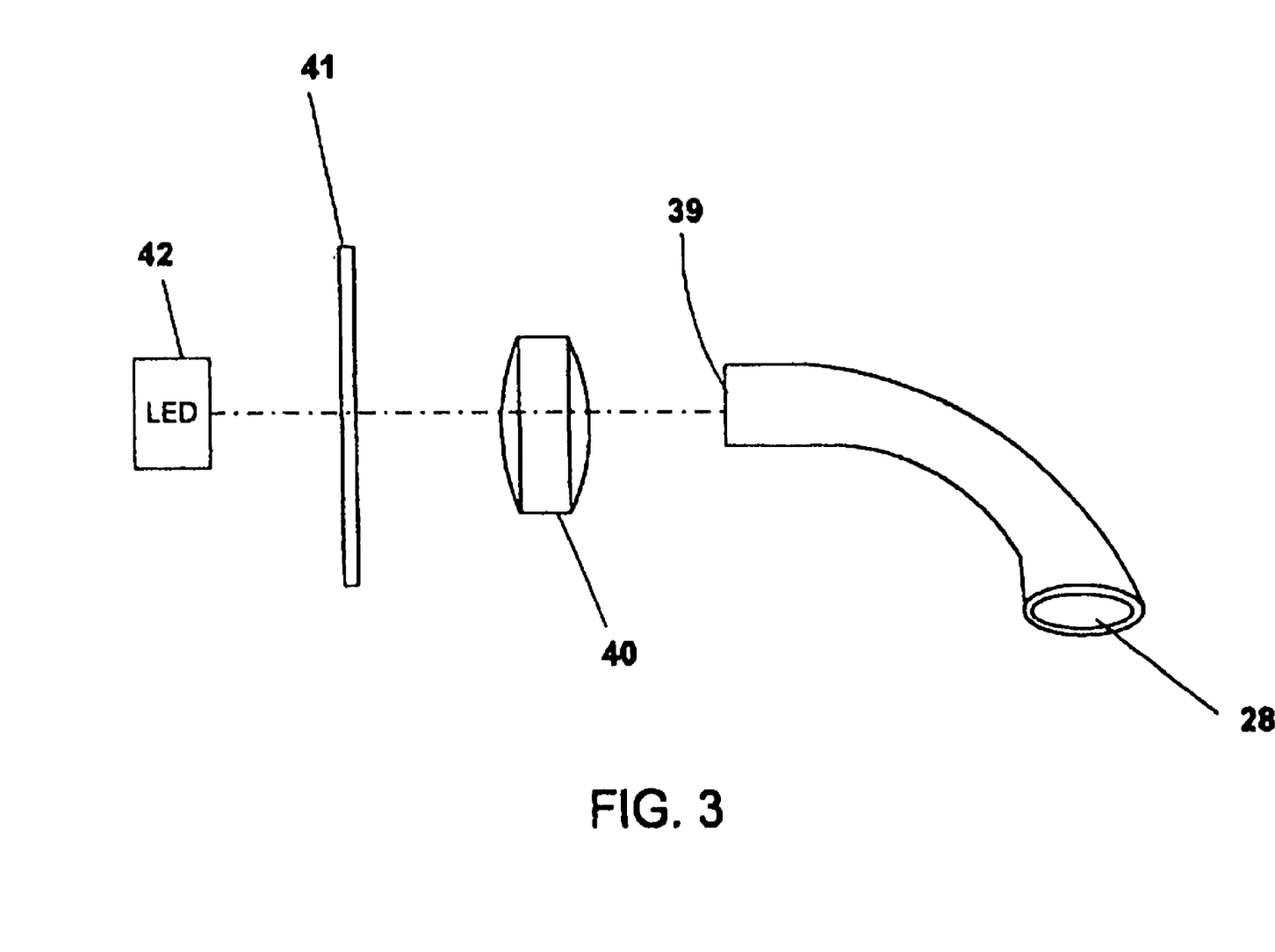
FIG. 3 is a drawing of a preferred ring light source.

As shown in FIG. 3, a light emitting diode (LED) module 42 consists of multiple white color LEDs could be used to provide light for the source 28. Alternatively other light sources such as flashed Xenon and Halogen could be used. The light is coupled into the entrance of fiber optical cable 39 by a lens 40 after passing through an optical filter 41 to properly adjust the color temperature of the light. The entrance of the fiber optical cable 39 has a shape similar to that of LED matrix on module 42. The exit of the fiber optical cable 39 forms a ring, which becomes the light source 28. The LED module 42 can work in either pulsed or continuous mode. When working in pulsed mode, the light pulse is synchronized with the trigger signals from the CCD camera. The change in the duration of the light pulse would adjust the brightness of the image, which is done automatically by the automatic exposure mechanism. Further compensation for the lighting condition can be adjusted manually if needed. If the light pulses are triggered consecutively by the imager, then a continuous illumination is perceived by the clinicians since the frequency of the pulses is higher than human eye can distinguish. When the interlaced CCD imager is used, the pulsed mode of illumination helps capture a single retinal picture to the computer with high speed and non-interlacing effect. Triggering a single light pulse synchronized with one of two fields for the captured image frame, and removing the light pulses before and immediately after that light pulse, will provide a full-frame image without the interlacing effect.

When working in the pulsed mode, the light pole is synchronized with the trigger signals from the CCD camera. The change in the duration of the light pulse would adjust the brightness of the image.

The LED module 42 can be moved out and replaced with the one consisting of multiple high power infrared or blue LEDs. These modules preferably provide light source for the FA and ICG sessions, and work in both continuous and pulsed mode similar to that of white color LED module. A blocking optical filter is inserted into the imaging path to block the excitation light.

The electronically controlled actuators behind the mirror 15 can tilt the mirror slightly along a axis within the paper plane, which in effect laterally moves the position of the optical aperture 19 and optical components from 20 to 23 and imager 18. A trigger signal from the electronic image sensor flashes the light source 28 and the computer records a digital image. As the mirror 15 is tilted to the opposite direction, a second image is taken. When the two images are displayed separately to left and right eyes of the clinician, a stereoscopic view of retina is created. The amount of tilt may be introduced to the mirror 16 in opposite direction to generate a more precise stereoscopic view.

Additional optical components enable the features of laser treatment. Laser 43A is guided to port 43 by an optical fiber 43B and passes through one of the pinholes on the pinhole array 44 that has pinholes of various sizes. Additional optics may be introduced between the port 43 and pinhole array 44 to homogenize the laser intensity. Lens 45 collimates the laser beam to lens 47, which in turn focuses the laser to the plane 14 and subsequently to the retina 9. The location of mirror 46 is conjugate to the entrance pupil of the optical system that is located at the eye lens of the patient. Mirror 46 may be rotated in two orthogonal axes in order to steer the laser beam across the retina. With the steering mirror located at a plane conjugate to the entrance pupil one can be assured that the laser light will inter the eye in a manner that the iris is not irradiated. A narrow band optical beam splitter (50) is inserted into the optical system to inject the laser light into the optical system while allowing the visual light passing though to the image sensor from the retina. The beam splitter 50 could also be a broad band polarization beam splitter, which reflects the s-polarized light only. The optical beam splitter 47 samples a small amount of laser light onto photo sensor 48 to determine the power of the laser light. With help of the image sensor the irradiance of the laser on retina can be determined.

In FIG. 2 the beam splitter 50 is located between mirror 17 and aperture 19. However, the beam splitter 50 can actually placed anywhere along the optical axis between the mirror 17 and image plane 14. The beam splitter 50 may be located between lens 30 and mirror 17 or between light source 28 and lens 29. The optical component 43 through 49 may function similarly in these alternative options.

In another variation, the laser may also be projected into the optical system from the space between light source 28, which is shaped as a ring, and mirror 17, which may be a dichroic beam splitter. In this instance the laser beam is injected in the middle of the illumination beam. Beam splitter 50 would be eliminated, but the optical components in the projection system from 44 through 49 would be kept.

During the process of laser therapy, the image sensor 18 or other detectors may detect the motion of the retina. The retinal image and the laser spot then can be stabilized by a servo system with two electrically activated actuators controlling the tilt of the mirror 16 and/or 17. Also, the laser spot may track the retinal image by controlling the tilt of mirror 46. Also, during the laser treatment the imaging system can be operated simultaneously. Thus, angiography can be performed simultaneous with treatment.

With a real-time image being displayed it would be possible for the clinician to mark on the displayed image the locus of the regions for intended treatment. The computer could then control the actual application of laser treatment with or without a manual or automatic tracking system.

Corneal Imaging

Figure 4:
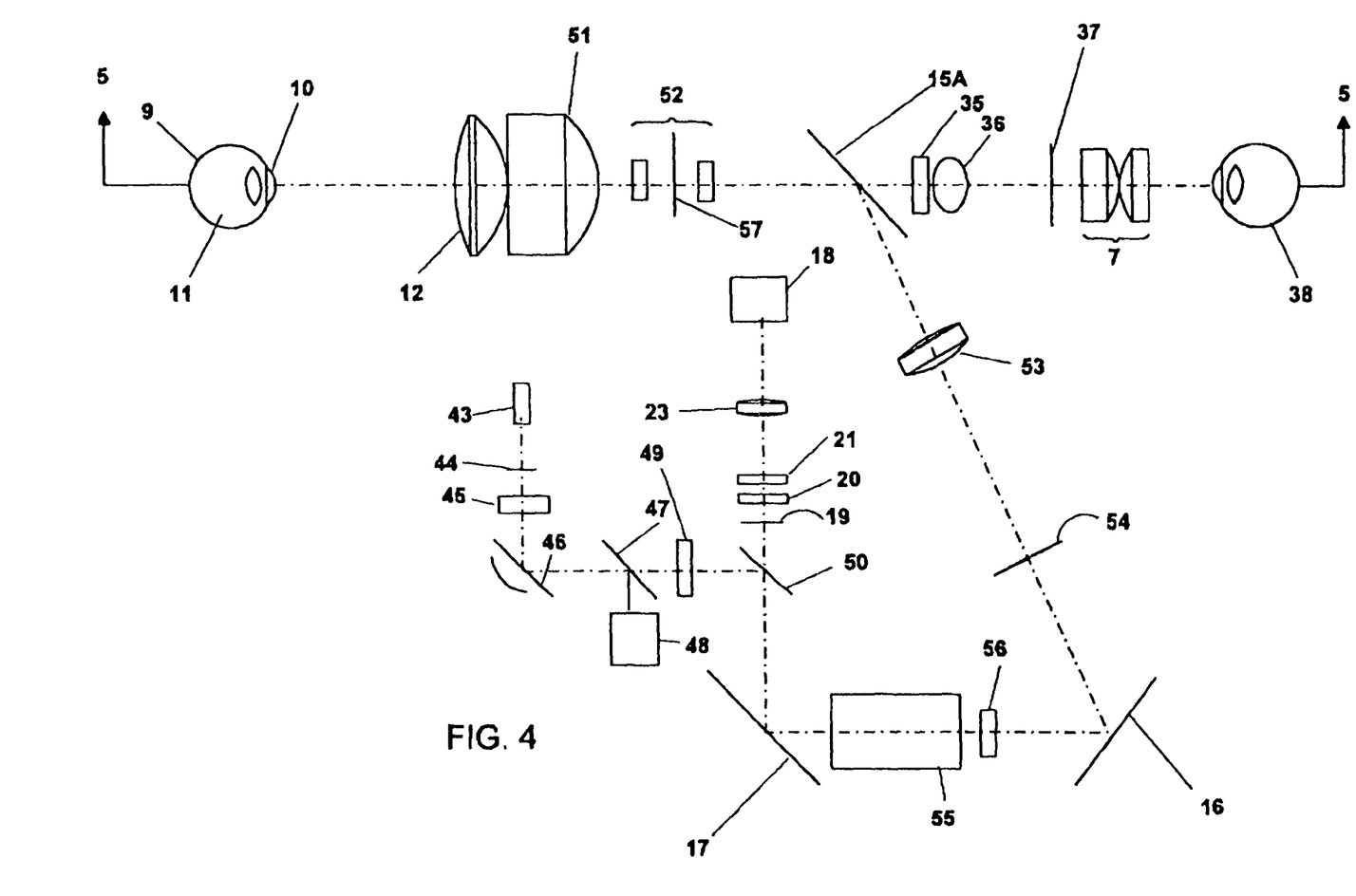
FIGS. 4, 4A, and 5 are drawings showing the corneal imaging portion of the preferred embodiment.
Figure 4A:
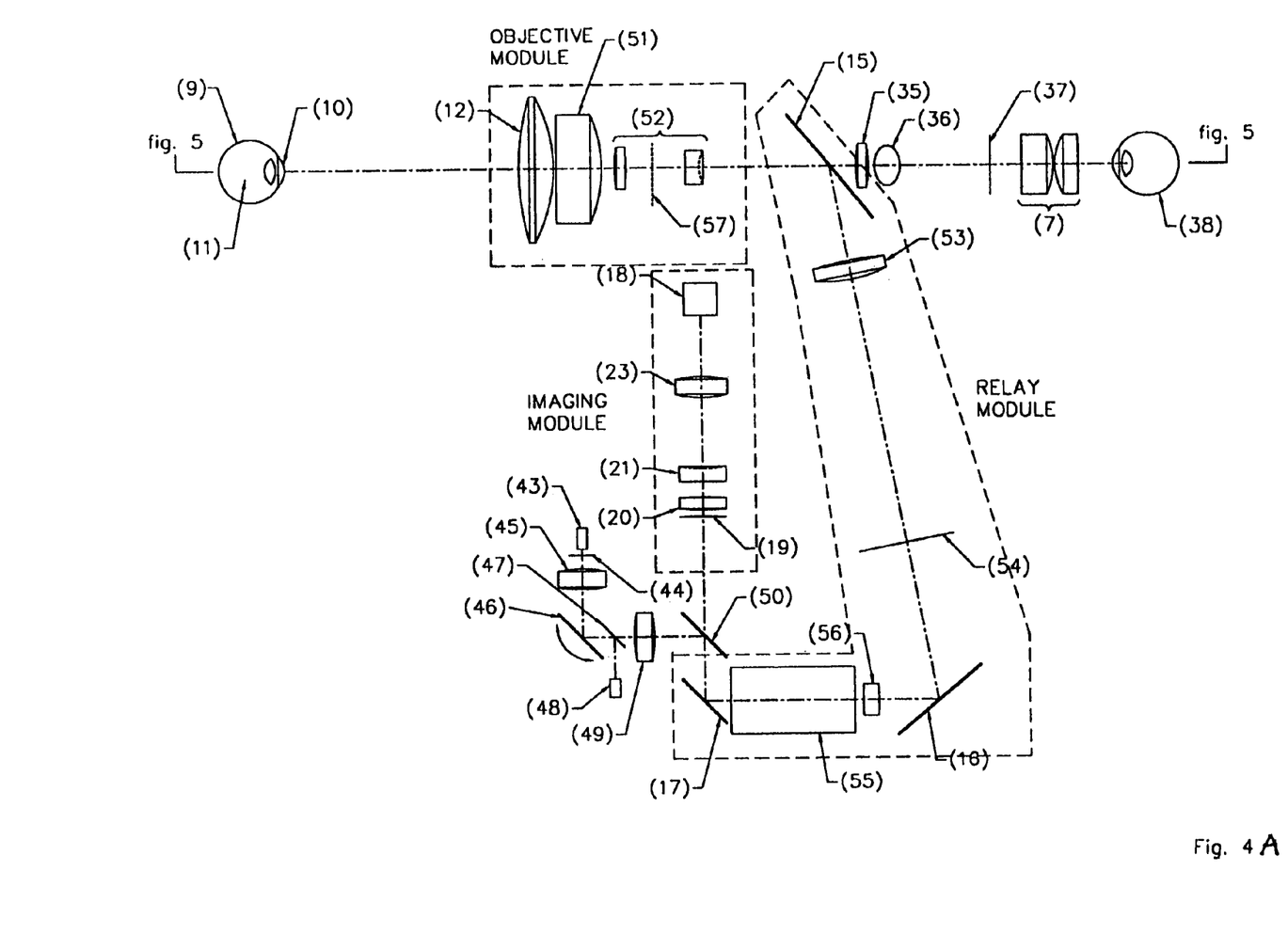
Figure 5:
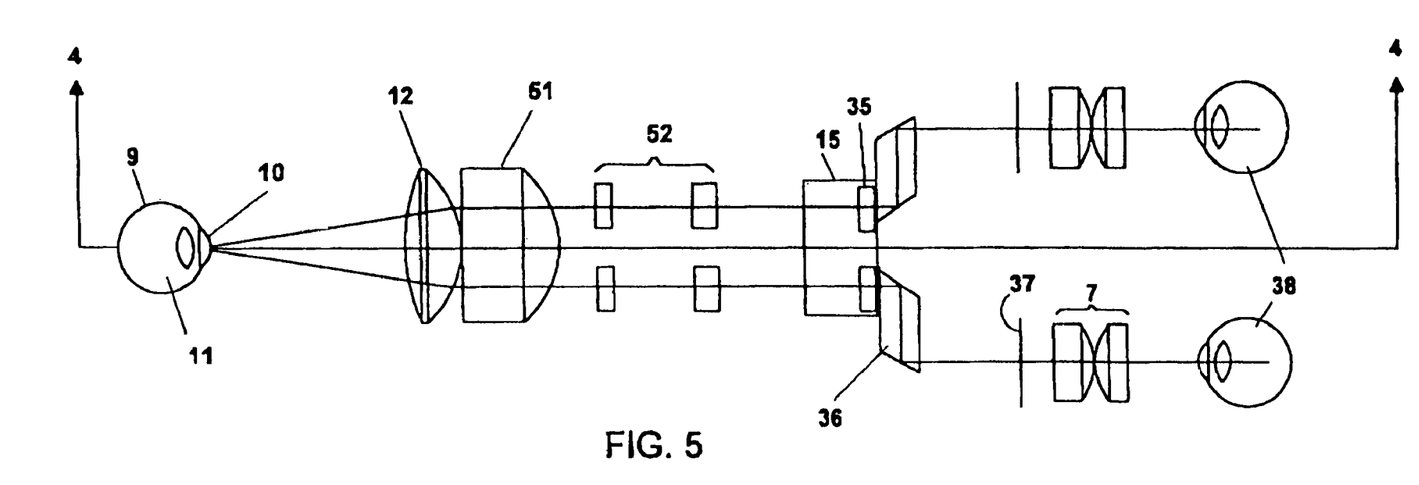

To describe this embodiment utilized for the corneal imaging reference is made to FIGS. 4 and 5. In FIG. 5 is shown a horizontal cross sectional view of the corneal imaging system in a plane on the optical axis line that includes the cornea 10. In FIG. 4 is shown a vertical cross sectional view of the corneal imaging system alone and through the middle of the system and in a plane which includes the cornea 10. In these figures the optics which are used for retinal imaging only have been moved out and replaced with those used for imaging and visualization of the anterior segment. The elements, which are changed between corneal and retinal imaging, include replacing mirror 15 with mirror 15A, adding elements 53, 55, 56, and 52, and replacing lens 13 with lens 51.

Optical lens 12 and 51 comprise the front and rear elements of the objective lens. Lens 12 is sealed in place and lens 13 used for retinal imaging is moved out and replaced with lens 51. Lens 12 and 51 together form the objective lens for the corneal imaging optical system and provide a virtual image of the cornea at image plane 57.

When imaging or visualizing the cornea is conducted, the objective lens set projects the object to infinity. The illumination of the cornea will be provided by the common means of a slit-lamp. Various lens sets 52 are inserted through an internal mechanism into the optical system and can be changed for higher or lower magnification as required. The individual axes of lenses in lens sets 52 are offset horizontally to the objective lens set to produce a stereo image. The lens sets 52 are afocal and can be reversed in direction to produce two magnifications for each lens set. The objective lens set redirects the individual optical axis of lens set 51 to converge at the center of the eye. By this means the corneal imaging system provides the proper look angle for stereoscopic vision.

Following lens set 52 is a mirror 15 that can be moved into the beam to direct the rays exiting the objective lens and magnification adjustment downwards to the digital imaging system located vertically below or removed to allow visualization of the cornea. The reflective coating on this mirror is designed to be highly reflective to laser light, but partially transmissive to the light of other wavelengths. In fact, this mirror can be a partial reflector to provide simultaneous visual observation with digital imaging and imaging simultaneous with laser treatment if desired.

For the visualization system, common erection prisms 36 follows image relay lens 35, as shown in FIG. 5. An inverted real image is formed at location 37. Lens sets 7 are common oculars or eyepieces and an erect image is formed at the retina of the user's eyes 38. The optical axes of the two ocular paths are shown to be in parallel in FIG. 5. However, the axes can be tilted to converge.

By changing lens set 52 a variety of magnifications are readily achieved and the eyepiece lens 7 can be exchanged as well for a wide range of magnifications.

When the corneal imaging system is to be used for digital imaging at least some of the light is reflected downwards by mirror 15. The light rays are relayed by lens 53 and 56 to form a virtual image of the cornea at plane 57. This is the same location for the image as produced by the retinal imaging system. This virtual image then can be projected to the image sensor 18 by the lens 20, 21 and 23. Lens 20 projects the image to infinity and lens 21 will make small adjustments to this and therefore accomplishes focusing. Lens 23 focuses the light onto the electronic camera 18.

Lens 53 and 56 are aligned to the optical axis of a single lens set 52 that is offset from the axis of lens 12 and 51 and image sensor 18. Prism set 55 is then used to translate the axis of the light beam from the offset axis to the centrally located axis of the CCD imaging system. The relay lens 53 and 56 not only form a real corneal image at plane 54, but also an entrance pupil of the imaging system at the front of lens set 52. This entrance pupil coincides with the one formed in the visualization system.

By moving the lens 53 to be aligned to the optical axis of another single lens set 52, and rotating the module consists of lens 56 and prism set 55 by 180.degree., the image from the other viewing channel can be recorded. When the two images are displayed separately to left and right eyes of the clinician, a stereoscopic view of anterior segment of eye is created. The stereoscopic effect is identical to that seen by naked eye from the binocular directly. Another stereoscopic approach would be to align the relay lens 53 and 56 to the centrally located axis of the CCD image system and eliminate the prism set 55. Electronically controlled actuators behind the mirror 15 could then tilt the mirror slightly along an axis within the paper plane which in effect moves the image position laterally and the optical aperture 19 and electronic imaging system behind it. Two images, taken from two oppositely tilted mirror positions, are recorded to and displayed by the computer to create the stereoscopic effect. Compared with the directly binocular visualization, the second approach introduces a tilt between the two viewing channels in the digital recording. As the result, the stereoscopic effect may be slightly different from that of the first approach. A third approach would tilt the mirror 16 in opposite direction from the tilt of mirror 15 to cancel out the unwanted effect. The result stereoscopic effect would be similar to that of the first approach.

A laser projection system identical with that used for the retinal laser system is formed by optical components 43 through 49 and projects laser to the cornea. The laser spot may either monitored from the image sensor alone or from both CCD camera and binoculars.

A slit lamp or other well-known means provides illumination of the eye. An LED module consists of multiple white LEDs can be used as the light source for the slit lamp. The light source works in either continuous or pulsed mode. When it works in pulsed mode, the light pulse is synchronized with the trigger signals from the CCD imager. A continuous illumination is then perceived by the clinicians since the frequency of the pulses is higher than human eye can distinguish. The brightness of the corneal image, observed either through the binocular or the CCD imager, is adjustable by changing the duration of the light pulse. When the interlaced CCD imager is used, the pulsed mode of illumination helps capturing a single corneal picture to the computer with high speed and non-interlacing effect. Triggering a single light pulse synchronized with one of two fields for the captured image frame, and removing the light pulses before and immediately after that light pulse does it.

Two Very Different Optical Configurations

The cornea is a slightly positively curved plane and the image path is air. The retina is a highly negatively curved plane and part of the optical path is the vitreous. This fluid is non-achromatic so the camera must compensate for the non-achromaticity of the media for the retina but not so for the air path for the cornea. The present invention achieves both of these functions, and at the high resolution required for ophthalmology as well as providing multiple magnifications.

Alignment with IR Camera

The system is designed to image the retina with low dilation. To achieve this, the first design criteria is to inject the light into the eye through a small ring about the entrance pupil and aligning this to the iris opening. Achieving this provides uniform illumination to the retina and a high contrast image. But, transverse and longitudinal alignments are critical. The use of an infrared camera operating at wavelengths that the eye cannot see is crucial. The infrared illumination does not cause the pupil to constrict. The IR camera is always on and focused on the cornea even while the retinal image is being obtained and a separate display shows this image. By this means the transverse and longitudinal alignment of the camera is always assured.

Entrance Pupil

Of further great challenge for the optical system is the requirement to have different camera entrance pupil locations for the corneal and retinal imaging functions. For imaging the retina, it is of significant advantage to place the entrance pupil of the camera at the eye lens. This reduces the effect of the aberrations of the eye and improves image contrast. However, for imaging the cornea, the entrance pupil must lie at the objective lens of the imaging system. The system thus operates as a "microscope" when imaging the cornea and as a "telescope" when imaging the retina.

Projecting Images Onto the Retina

Of further functional advantage is that the system provides a plane in the instrument that is conjugate to the retina and this plane lies on the surface of the electronic image sensor. With certain optical beam splitters, this plane can be made accessible within the instrument at other locations for other uses. It is recognized that light emerging from the retina will return to and be in focus on this conjugate plane and this is the modality for imaging. However, light exiting from a plane conjugate to the retina and directed towards the eye will be projected onto the retina. Thus, we have within the system the ability to project light patterns onto the retina. The system could be used for testing the performance of the eye as an imaging system. A simple example of this would be to project visual acuity charts or color perception information. A more complex application would be to perform perimetric measurements. In fact, a programmable LCD could be used to modify the stimulus.

LED Module

White color LED modules consist of multiple LEDs will be used as the light sources in both retinal imaging and corneal imaging part of the system. The LED module works either continuously or in pulsed mode. It will replace the CW light source (often halogen lamp) and flash source (often Xenon lamp) with one single source. It consumes less power, generates less heat, use less housing space, and last much longer. LED modules with different wavelengths will be used as light source for FA and ICG angiograms.

Stereoscopic Images

The stereoscopic images of optic nerve head have shown great clinic values in assessing the progress of diseases like glaucoma. The proposed system can take two digital images of optic nerve head from two different entrance pupil positions automatically in less than $1/10$ of second. When the two images are displayed separately into left and right eyes, the clinician then sees and perceives the stereoscopic views of the optic nerve head. The stereoscopic corneal images can also be taken and displayed digitally. The proposed system can also take two digital images of anterior segment of the eye automatically in very short time, display stereoscopic view digitally.

Laser Treatment

One of the major treatment modalities in eye health-care is to apply laser energy to destroy portions of the retina or iris, and, with the new photodynamic therapies, stimulate a pharmaceutical to cause the curative effect. The proposed system provides an internally integrated laser projection system. The laser light can be projected internally from a plane conjugate to the imaging plane. No external optics or attachment is needed. The hand of clinician is free from holding the laser lens. There will be no more scattering of laser light from external optics. With the help of the infrared alignment system, the alignment is easy and simple. When the system is switched to the retinal imaging mode, the laser beam with the appropriate beam characteristic would reach the retina. The illumination to the retina is provided internally and independent of the positions of laser beam. Free from the glazing light reflection from the optics and cornea, the retinal image is much clearer. When the system is switched to the corneal imaging mode, the laser would be delivered to the corneal region. In fact, with the imaging system functioning in a real-time mode, the operator can observe the retinal/corneal image with aiming laser spot on them, then designate (on the image as presented by the computer) the areas to be treated. The system, under computer control, could apply the laser treatment. In the instance of some laser treatments, over 1,000 spots are applied. Performing this manually is very slow but performing it under computer control could be accomplished quickly and accurately. Further, tracking systems could be used to further stabilize the image and/or the laser beam location. The location and accumulated energy delivery as a function of location can be determined and monitored, which is important parameter in some therapies.

Other Advantages

Because the system alignment, retinal/corneal image and aiming laser spot can be monitored and manipulated in real time remotely, the clinician is free from the restricted posture during the treatment session, which is the case in the current slit-lamp delivery system. It would greatly reduce the stress imposed on the patients and clinicians.

Further, this system can perform the popular flourescein and indocyanine green angiographies. Even the stereo angiograms can be recorded and displayed digitally. In fact, as discussed below, the system is equipped to utilize the differing format sensors that may be preferred for color or monochrome imaging. The angiographic images can be displayed with known scales to help determining the position and size of laser treatment areas. During the treatment, the angiographic images can be displayed side-by-side with the live images of same scale on one computer monitor. It will greatly reduce the time and preparation work before a laser treatment. Laser treatments can be accomplished simultaneously with angiography. This gives the clinician the ability to identify the area for treatment and monitor in real time the effect of the laser treatment.

As noted, digital imaging obviously eliminates the delay and cost of film processing and assessment of image quality is immediately available. As an example of the value of examining images vs. direct visualization, studies have shown that in screening for diabetic retinopathy, a better result is obtained by examining images rather than the direct visualization. However, digital imaging brings other substantial advantages. One of the most prominent is the ability to share findings with colleges and the like by digital transference means. That is, the actual clinical data may be obtained at one location and sent to another by electronic means for remote assessment. If one could examine the entire eye by digital means, a clinical assistant at a remote site could obtain the "digital copy" of the eye and transfer it to the appropriate clinical expert for review. Such a system would clearly need to image both the posterior and anterior segments of the eye and with high quality images.

With this system there is no need to perform an ophthalmoscopic exam unless the far peripheral of the eye is to be examined. This is not routinely done in most eye exams and is only relevant for populations with substantially increased risk factors. However, documenting the posterior pole would be of great value for all patients. Accordingly, the time for an examination would be reduced.

While the present invention has been described in terms of preferred embodiments, the reader should understand that the invention is not limited to those preferred embodiments. Therefore the invention is to be determined by the appended claims and their legal equivalents.

What is claimed is:

1. An apparatus for illuminating and viewing the anterior segment of an eye of a patient comprising:
   a binocular microscope having an optical axis;
   an electronic sensor;
   an electronic display coupled to display an image captured by the electronic sensor;
   a slit lamp utilizing a light emitting diode (LED) configured as a source of light to illuminate the anterior segment of an eye of a patient when forming an image of the anterior segment of an eye of a patient; and
   a beam directing element configured to transmit a first part of light returned from the anterior segment of an eye of a patient along the optical axis of the binocular microscope and to direct a second part of light returned from the anterior segment of an eye of a patient to the electronic sensor to allow viewing of the image on the electronic display and visual observation through the binocular microscope of the anterior segment of an eye of a patient.

2. The apparatus for illuminating and viewing the anterior segment of an eye of a patient of claim 1 where:
   the LED is configured to operate in either pulsed or continuous mode.

3. The apparatus for illuminating and viewing the anterior segment of an eye of a patient of claim 1 where the electronic sensor comprises:
   an image sensor that receives or generates trigger pulses; and
   with the LED configured to be pulsed in synchronism with the trigger pulses when operating in the pulsed mode.

4. The apparatus for illuminating and viewing the anterior segment of an eye of a patient of claim 1 where the brightness and color of the LED are adjustable.

5. The apparatus for illuminating and viewing the anterior segment of an eye of a patient of claim 4 where:
   the LED brightness is adjustable by changing the duration of the light pulse.

6. The apparatus for illuminating and viewing the anterior segment of an eye of a patient of claim 1 further comprising:
   LEDs of different wavelengths to facilitate performing FA and ICG angiograms.

7. The apparatus for illuminating and viewing the anterior segment of an eye of a patient of claim 1 where the LED is a white color LED.

8. The apparatus for illuminating and viewing the anterior segment of an eye of a patient of claim 1 where:
   the beam directing element is disposed on the optical axis of the binocular microscope and is partially reflective to direct the second part of light returned from the anterior segment of an eye of a patient to the electronic sensor.

9. A method for illuminating and viewing the anterior segment of an eye of a patient comprising:
   directing illumination, using a slit lamp, at the anterior segment of an eye of a patient, with the illumination produced by a light emitting diode (LED) used as a source of light of the slit lamp to illuminate the anterior segment of an eye of a patient when forming an image of the anterior segment of an eye of a patient;
   transmitting a first part of light returned from the anterior segment of an eye of a patient along the optical axis of a binocular microscope to allow visual observation of the anterior segment of an eye of a patient;
   directing a second part of light returned from the anterior segment of an eye of a patient toward an electronic sensor to allow digital imaging of the anterior segment of an eye of a patient; and
   displaying an image of the anterior segment of an eye of a patient captured by the electronic sensor on an electronic display to allow viewing of the anterior segment of an eye of a patient on the electronic display.

10. The method of claim 9 further comprising:
operating the LED in either pulsed or continuous mode.

11. The method of claim 10 where illumination from the pulsed LED is perceived as continuous when the trigger frequency is higher than a human eye can distinguish.

12. The method of claim 11 further comprising:
adjusting the brightness of the LED by changing the duration of the light pulse.

13. A method for illuminating and viewing the anterior segment of an eye of a patient comprising:
directing illumination, using a slit lamp, at the anterior segment of an eye of a patient, with the illumination produced by a pulsed light emitting diode (LED) used as a source of light of the slit lamp to illuminate the anterior segment of an eye of a patient when forming an image of the anterior segment of an eye of a patient, where the image is used for examination of the anterior segment of an eye of a patient;
transmitting a first part of light returned from the anterior segment of an eye of a patient along the optical axis of a binocular microscope to allow visual observation of the anterior segment of an eye of a patient;
directing a second part of light returned from the anterior segment of an eye of a patient toward an electronic sensor to allow digital imaging of the anterior segment of an eye of a patient;
displaying an image of the anterior segment of an eye of a patient captured by the electronic sensor on an electronic display to allow viewing of the image on the electronic display; and
pulsing the LED in synchronism with trigger pulses used to trigger the electronic sensor.

14. The method of claim 13 where live images from the electronic sensor are perceived as continuous when the trigger frequency is the same as or higher than the frame rate of the electronic sensor.

15. The method of claim 14 further comprising:
adjusting image brightness by changing the duration of the light pulse.

16. A method for illuminating and viewing the anterior segment of an eye of a patient comprising:
directing illumination, using a slit lamp, at the anterior segment of an eye of a patient, with the illumination produced by a pulsed light emitting diode (LED) used as a source of light of the slit lamp to illuminate an eye of a patient when forming an image of the anterior segment of an eye of a patient, where the image is used for examination of the anterior segment of an eye of a patient;
transmitting a first part of light returned from the anterior segment of an eye of a patient along the optical axis of a binocular microscope to allow visual observation of the anterior segment of an eye of a patient;
directing a second part of light returned from the anterior segment of an eye of a patient toward a CCD image sensor to allow digital imaging of the anterior segment of an eye of a patient;
displaying an image of the anterior segment of an eye of a patient captured by the CCD image sensor on an electronic display to allow viewing of the image on the electronic display of the anterior section of an eye of a patient; and
pulsing the LED in synchronism with trigger pulses used to trigger the CCD image sensor.

17. The method of claim 16, where illumination from the pulsed LED is perceived as continuous under observation through the binocular microscope when the trigger frequency is higher than a human eye can distinguish.

18. The method of claim 16 where live images from the CCD image sensor are perceived as continuous when the trigger frequency is the same as or higher than the frame rate of the CCD image sensor.

19. The method of claim 16 further comprising:
adjusting illumination brightness of the LED by changing the duration of the light pulse.

20. An apparatus for illuminating and viewing the anterior segment of an eye of a patient comprising:
a binocular microscope having an optical axis;
an electronic senor;
an electronic display coupled to display an image captured by the electronic sensor;
a slit lamp utilizing a light emitting diode (LED) configured as a source of light to illuminate the anterior segment of an eye of a patient when forming an image of the anterior segment of an eye of a patient; and
a beam directing element configured to be inserted into a light beam returned from the anterior segment of an eye of a patient, with the light beam directed along the optical axis of the binocular microscope, to direct the light beam returned from the anterior segment of an eye of a patient to the electronic sensor to allow viewing of the image on the electronic display when the beam directing element is inserted and to allow visual observation through the binocular microscope of the anterior segment of an eye of a patient when the beam directing element is not inserted.

21. The apparatus for illuminating and viewing the anterior segment of an eye of a patient of claim 20 where the brightness and color of the LED are adjustable.

22. The apparatus for illuminating and viewing the anterior segment of an eye of a patient of claim 21 where:
the LED brightness is adjustable by changing the duration of the light pulse.

23. The apparatus for illuminating and viewing the anterior segment of an eye of a patient of claim 20 further comprising:
LEDs of different wavelengths to facilitate performing FA and ICG angiograms.

24. The apparatus for illuminating and viewing the anterior segment of an eye of a patient of claim 20 where the LED is a white color LED.

25. A method for illuminating and viewing the anterior segment of an eye of a patient comprising:
directing illumination, using a slit lamp, at the anterior segment of an eye of a patient, with the illumination produced by a light emitting diode (LED) used as a source of light of the slit lamp to illuminate the anterior segment of an eye of a patient when forming an image of the anterior segment of an eye of a patient;
transmitting a light beam returned from the anterior segment of an eye of a patient along the optical axis of a binocular microscope to allow visual observation of the anterior segment of an eye of a patient;
inserting a beam directing element into the light beam returned from the anterior segment of an eye of a patient to direct the light beam toward an electronic sensor to allow digital imaging of the anterior segment of an eye of a patient; and
displaying an image of the anterior segment of an eye of a patient captured by the electronic sensor on an electronic display to allow viewing of the anterior segment of an eye of a patient on the electronic display.

26. A method for illuminating and viewing the anterior segment of an eye of a patient comprising:
- directing illumination, using a slit lamp, at the anterior segment of an eye of the patient, with the illumination produced by a pulsed light emitting diode (LED) used as a source of light of the slit lamp to illuminate the anterior segment of an eye of a patient when forming an image of the anterior segment of an eye of a patient, where the image is used for examination of the anterior segment of an eye of a patient;
- transmitting a light beam returned from the anterior segment of an eye of a patient along the optical axis of a binocular microscope to allow visual observation of the anterior segment of an eye of a patient;
- inserting a beam directing element into the light beam returned from the anterior segment of an eye of a patient to direct the light beam toward an electronic sensor to allow digital imaging of the anterior segment of an eye of a patient;
- displaying an image of the anterior segment of an eye of a patient captured by the electronic sensor on an electronic display to allow viewing of the image on the electronic display; and
- pulsing the LED in synchronism with trigger pulses used to trigger the electronic sensor.

27. A method for illuminating and viewing the anterior segment of an eye of a patient comprising:
- directing illumination, using a slit lamp, at the anterior segment of an eye of patient, with the illumination produced by a pulsed light emitting diode (LED) used as a source of light of the slit lamp to illuminate an eye of a patient when forming an image of the anterior segment of an eye of a patient, where the image is used for examination of the anterior segment of an eye of a patient;
- transmitting a light beam returned from the anterior segment of an eye of a patient along the optical axis of a binocular microscope to allow visual observation of the anterior segment of an eye of a patient;
- inserting a beam directing element into the light beam returned from the anterior segment of an eye of a patient to direct the light beam toward a CCD image sensor to allow digital imaging of the anterior segment of an eye of a patient;
- displaying an image of the anterior segment of an eye of a patient captured by the CCD image sensor on an electronic display to allow viewing of the image on the electronic display; and
- pulsing the LED in synchronism with trigger pulses used to trigger the CCD image sensor.

* * * * *